US008512224B2

(12) United States Patent
Li et al.

(10) Patent No.: US 8,512,224 B2
(45) Date of Patent: *Aug. 20, 2013

(54) METHOD OF PRODUCING AN INSEMINATE

(75) Inventors: Xihe Li, Huhhot (CN); Wenzhong Zhou, Beijing (CN); Guofu Zhang, Huhhot (CN); Songjin Qian, Tongliao (CN); Jianguo Wang, Huhhot (CN)

(73) Assignee: XY, LLC, Navasota, TX (US)

(*) Notice: Subject to any disclaimer, the term of this patent is extended or adjusted under 35 U.S.C. 154(b) by 848 days.

This patent is subject to a terminal disclaimer.

(21) Appl. No.: 12/587,909

(22) Filed: Oct. 15, 2009

(65) Prior Publication Data

US 2010/0191042 A1    Jul. 29, 2010

Related U.S. Application Data

(63) Continuation-in-part of application No. 12/321,704, filed on Jan. 24, 2009, now Pat. No. 8,251,887.

(51) Int. Cl.
A61D 7/00 (2006.01)
A01D 1/00 (2006.01)
A01N 1/02 (2006.01)

(52) U.S. Cl.
USPC .................................. 600/35; 435/1.1; 435/2

(58) Field of Classification Search
USPC ......................................... 600/35; 435/1.1, 2
See application file for complete search history.

(56) References Cited

U.S. PATENT DOCUMENTS

| | | | |
|---|---|---|---|
| 4,267,268 A | 5/1981 | Nelson, Jr. | |
| 4,312,350 A * | 1/1982 | Doan | 604/349 |
| 4,362,246 A | 12/1982 | Adair | |
| 5,135,759 A | 8/1992 | Johnson | |
| 5,770,363 A | 6/1998 | Brown | |
| 5,972,592 A | 10/1999 | Suarez | |
| 6,071,689 A | 6/2000 | Seidel et al. | |
| 6,103,481 A * | 8/2000 | Schatten et al. | 435/7.21 |
| 6,149,867 A | 11/2000 | Seidel et al. | |
| 6,372,422 B1 | 4/2002 | Seidel et al. | |
| 6,524,860 B1 | 2/2003 | Seidel et al. | |
| 7,070,917 B1 * | 7/2006 | Christensen et al. | 435/2 |
| 7,094,527 B2 | 8/2006 | Seidel et al. | |
| 7,169,548 B2 | 1/2007 | Maxwell et al. | |
| 7,195,920 B2 | 3/2007 | Seidel et al. | |
| 7,208,265 B1 | 4/2007 | Schenk | |
| 7,221,453 B2 | 5/2007 | Sharpe et al. | |
| 7,371,517 B2 | 5/2008 | Evans et al. | |
| 7,772,005 B1 * | 8/2010 | Squires et al. | 436/63 |
| 8,251,887 B2 * | 8/2012 | Li et al. | 600/35 |
| 2005/0053910 A1 | 3/2005 | McKenzie et al. | |
| 2006/0121440 A1 | 6/2006 | Schenk et al. | |

FOREIGN PATENT DOCUMENTS

| | | |
|---|---|---|
| CN | 1732983 A | 2/2006 |
| CN | 1927226 A | 3/2007 |
| CN | 101220345 A | 7/2008 |
| JP | 2008-63235 | 3/2008 |

OTHER PUBLICATIONS

Definition of "Heterogeneous" found in the Merian-Webster dictionary (Online on : Jun. 14, 2012).*
Napier Fertility in the male rabbit..Journal of Reproduction and Fertility 2 :273 (1961).*
Foote, R.H., The history of Artificial insemination : Selected notes and notables. Published by the American Society of Animal Science in 2002.*
Suquet et al. Cryopreservation of Sperm in Marine Fish. Aquaculture Research by Blackwell Publishing, Inc. [http://www.ifremer.fr/docelec (30 pages)] vol. 31 No. 3 : pp. 231-243 (Mar. 2000).*
Wang et al. Study on Application of Frozen Sexed X-Semen of Dairy Cow. Journal of Guangxi Agric. and Biol. Science, vol. 25, Sep. 2006, p. 192. http://www.beefsemenonline.co.uk/misc/highfertility.htm, High Fertility Semen, World Class Genetics Beef Semen Online, Mixed Semen, printed Mar. 11, 2009 (one page).*
Yassem et al., Freezability of Bovine Spermatozoa in Tris-Buffered Yolk Extenders Containing Different Levels of Tris, Sodium, Potassium and Calcium Ions. Journal of Dairy Science 50(6) : 887-892 (1967).*
Vogt, P. H., et al.; "Human Y Chromosome Azoospermia Factors (AZF) Mapped to Different Subregions in Yq11"; Article, 1996, pp. 933-943, vol. 5, No. 7, Human Molecular Genetics, Oxford University Press USA (11 pages).
Tiersch, Terrence R.; "Strategies for Commercialization of Cryopreserved Fish Semen"; Article, 2008, pp. 15-19, vol. 37, R. Bras. Zootec (5 pages).
Foote, R.H., "Buffers and Extenders: What Do They Do? Why Are They Important?"; Article, 1984, pp. 62-70, Proc of the NAAB Tech. Conf. on Artificial Insemination and Reproduction (9 pages).
US Office Action dated Feb. 13, 2012 issued in corresponding U.S. Appl. No. 12/321,704 (19 pages).
Baccetti, Baccio, et al.; "Infertile Spermatozoa in a Human Carrier of Robertsonian Translocation 14;22"; Article, Nov. 2002; pp. 1127-1130, vol. 78, No. 5; Fertility and Sterility, USA (4 pages).

(Continued)

*Primary Examiner* — Ethan C Whisenant
(74) *Attorney, Agent, or Firm* — Ryan Christensen; Cindee R. Ewell

(57) ABSTRACT

A reduced dose inseminate and method for producing and using such reduced dose inseminate to fertilize the eggs of a female animal by artificial insemination with fewer sperm cells than compared with conventional dose inseminates.

17 Claims, 3 Drawing Sheets

(56) References Cited

OTHER PUBLICATIONS

Garner, D. L., et al.; "Seminal Plasma Addition Attenuates the Dilution Effect in Bovine Sperm"; Article, Mar. 5, 2001, pp. 31-40, vol. 56, Theriogenology, USA (10 pages).

Kaeoket, Kampon, et al.; "A Preliminary Study on Using Autologous and Heterologous Boar Sperm Supernatant from Freezing processed as Post-Thawing Solution: Its Effect on Sperm Motility"; Article, 2011, pp. 1049-1055, vol. 43, Trop Anim Health Prod., Springer (7 pages).

Parks, John E., et al.; "Cryopreservation of Peregrine Falcon Semen and Post-Thaw Dialysis to Remove Glycerol"; Article, 1986, pp. 15-20, vol. 20, Raptor Research USA (5 pages).

Perez-Garnelo, S. S., et al.; "Post-Thaw Viability of European Bison (*Bison bonasus*) Semen Frozen with Extenders Containing Egg Yolk or Lipids of Plant Origin and Examined With a Heterologous in vitro Fertilization Assay"; Article, 2006, pp. 116-125, vol. 37 No. 2, Journal of Zoo and Wildlife Medicine, USA (11 pages).

Roth, Terri L., et al.; "Scimitar-Horned Oryx (*Oryx dammah*) Spermatozoa are Functionally Competent in a Heterologous Bovine In Vitro Fertilization System After Cryopreservation on Dry Ice, in a Dry Shipper, or over Liquid Nitrogen Vapor"; Article, 1999, pp. 493-498, vol. 60, Biology of Reproduction USA (6 pages).

U.S. Appl. No. 10/081,955, filed Feb. 20, 2002.
U.S. Appl. No. 10/556,981, filed Nov. 15, 2005.
U.S. Appl. No. 10/398,796, filed Apr. 3, 2003.
U.S. Appl. No. 10/879,480, filed Jun. 21, 2001.
U.S. Appl. No. 10/523,268, filed Jan. 31, 2005.
U.S. Appl. No. 10/522,320, filed Jan. 24, 2005.
U.S. Appl. No. 10/524,793, filed Feb. 15, 2005.
U.S. Appl. No. 11/219,607, filed Sep. 2, 2005.
U.S. Appl. No. 11/004,382, filed Dec. 3, 2004.
U.S. Appl. No. 11/536,576, filed Sep. 28, 2006.
PCT Patent Application No. PCT/US2006/013082, filed Apr. 6, 2006.
U.S. Appl. No. 11/608,079, filed Dec. 7, 2006.
U.S. Appl. No. 11/608,039, filed Dec. 7, 2006.
U.S. Appl. No. 11/508,133, filed Aug. 21, 2006.
U.S. Appl. No. 11/536,492, filed Sep. 28, 2006.
U.S. Appl. No. 11/613,605, filed Dec. 20, 2006.
PCT Patent Application No. PCT/US2006/028846, filed Jul. 24, 2006.
U.S. Appl. No. 11/442,735, filed May 25, 2006.
U.S. Appl. No. 11/668,148, filed Jan. 29, 2007.
U.S. Appl. No. 11/400,839, filed Apr. 6, 2006.
U.S. Appl. No. 11/804,879, filed May 21, 2007.
PCT Patent Application No. PCT/US2007/014724, filed Jun. 26, 2007.
U.S. Appl. No. 11/805,572, filed May 22, 2007.
U.S. Appl. No. 10/812,351, filed Mar. 29, 2004.
U.S. Appl. No. 10/811,593, filed Mar. 29, 2004.
U.S. Appl. No. 11/092,509, filed Mar. 29, 2005.
U.S. Appl. No. 11/092,313, filed Mar. 29, 2005.
U.S. Appl. No. 11/572,376, filed Jul. 22, 2005.
U.S. Appl. No. 11/092,338, filed Mar. 29, 2005.
U.S. Appl. No. 12/113,684, filed May 1, 2008.
U.S. Appl. No. 10/266,562, filed Oct. 7, 2002.
PCT Patent Application No. PCT/US2005/043926, filed Dec. 2, 2005.

Azmal, S.A. et al., Relative Merits of Homo and Heterospermic Bull Semen in Respect of Preservation Quality, Pakistan Journal of Biological Sciences 7(11), 2004, pp. 1908-1911.

Beatty, R.A., Fertility of Mixed Semen From Different Rabbits, Journal of Reprod. Fertil., 1960, vol. 1, pp. 52-60.

Ryder, Neil, Genus mixed-semen service increases conception rates, Farmers Guardian, Jan. 17, 2003, pg. 70 (two total printed pages).

Liu et al., "Research Progress of Factors Affecting the Quality of Silage", China Cattle Science, vol. 32 No. 5, Sep. 2006, pp. 59-66.

Moussa et al., "Low density lipoproteins extracted from hen egg yolk by an easy method: cryoprotective effect on frozen-thawed bull semen", Theriogenology 57, 2002, pp. 1695.

Tartaglione et al., "Prognostic value of spermatological parameters as predictors of in vitro fertility of frozen-thawed bull semen", Theriogenology 62, 2004, pp. 1245-1252.

\* cited by examiner

METHOD OF PRODUCING AN INSEMINATE

This United States non-provisional patent application is a continuation-in-part of U.S. patent application Ser. No. 12/321,704, filed Jan. 24, 2009, hereby incorporated by reference herein.

I. BACKGROUND

Artificial insemination of female animals and in vitro fertilization of oocytes with fresh or frozen-thawed semen have been applied to the reproduction of animals. According to the traditional theory and conventional procedures, a great number of sperm cells are needed to ensure a successful fertilization.

However, semen from certain animals and sex-selected inseminates which are produced by separating X-chromosome bearing sperm cells from Y-chromosome bearing sperm cells can be in limited supply. Additionally, the sperm cells of certain animals and sex-selected inseminates can have reduced fertility or cannot achieve the threshold of fertility in the context of conventional procedures for successful fertilization. In the cases of limited specific genetic resources, or the suspension of spermatozoa of the semen can not reach the threshold of fertility, a complementary technology may be needed to solve the problems.

Additionally, semen from certain animals and sex-selected inseminates when frozen by conventional methods and then thawed can have a substantially reduced motility, percent intact acrosomes and survival time all of which can militate against successful use of frozen-thawed semen and sex-selected inseminates for artificial insemination of female animals.

The inventive reduced dose inseminate (or low dose inseminate) described-herein addresses each of the above-described problems.

II. SUMMARY OF THE INVENTION

Accordingly, a broad object of the invention can be to provide a method for producing and using a reduced dose inseminate to fertilize the eggs of a female animal by artificial insemination with fewer sperm cells than compared with conventional dose inseminates.

Another broad object of the invention can be to provide a reduced dose inseminate which includes fewer sperm cells to achieve fertilization by conventional artificial insemination which increases the usage of rare genetic resources and lowers the cost of embryo production.

Another broad object of the invention can be to provide a reduced dose inseminate to treat infertility due to low numbers of sperm cells or low numbers of fertile sperm cells, or poor activity of sperm cells.

Another broad object of the invention can be to provide a method of producing, freezing and thawing a reduced dose inseminate to increase post thaw motility, percent intact acrosomes, and survival time to correspondingly increase the length of time in which frozen thawed sperm cells can be used for artificial insemination and increase conception rates.

Naturally, further objects of the invention are disclosed throughout other areas of the specification, drawings, photographs, and claims.

III. A BRIEF DESCRIPTION OF THE DRAWINGS

IV. DETAILED DESCRIPTION OF THE PREFERRED EMBODIMENTS

Generally, a reduced dose inseminate produced by combining an amount of paternal semen of a paternal animal with an amount of heterogeneous semen of a heterogeneous male animal, the combination capable of fertilizing an egg of a female animal of the species of the paternal animal and methods of producing and using the reduced dose inseminate for in vivo or in vitro fertilization for the production of embryos and offspring of the species of the paternal animal.

Specifically, a reduced dose inseminate produced by combining a plurality of paternal sperm cells obtained from a paternal mammal with a plurality of heterogeneous sperm cells obtained from a heterogeneous animal and methods of producing and using the reduce dose inseminate for the in vivo and in vitro fertilization for the production of embryos and offspring of the species of the paternal animal.

Figure 1:
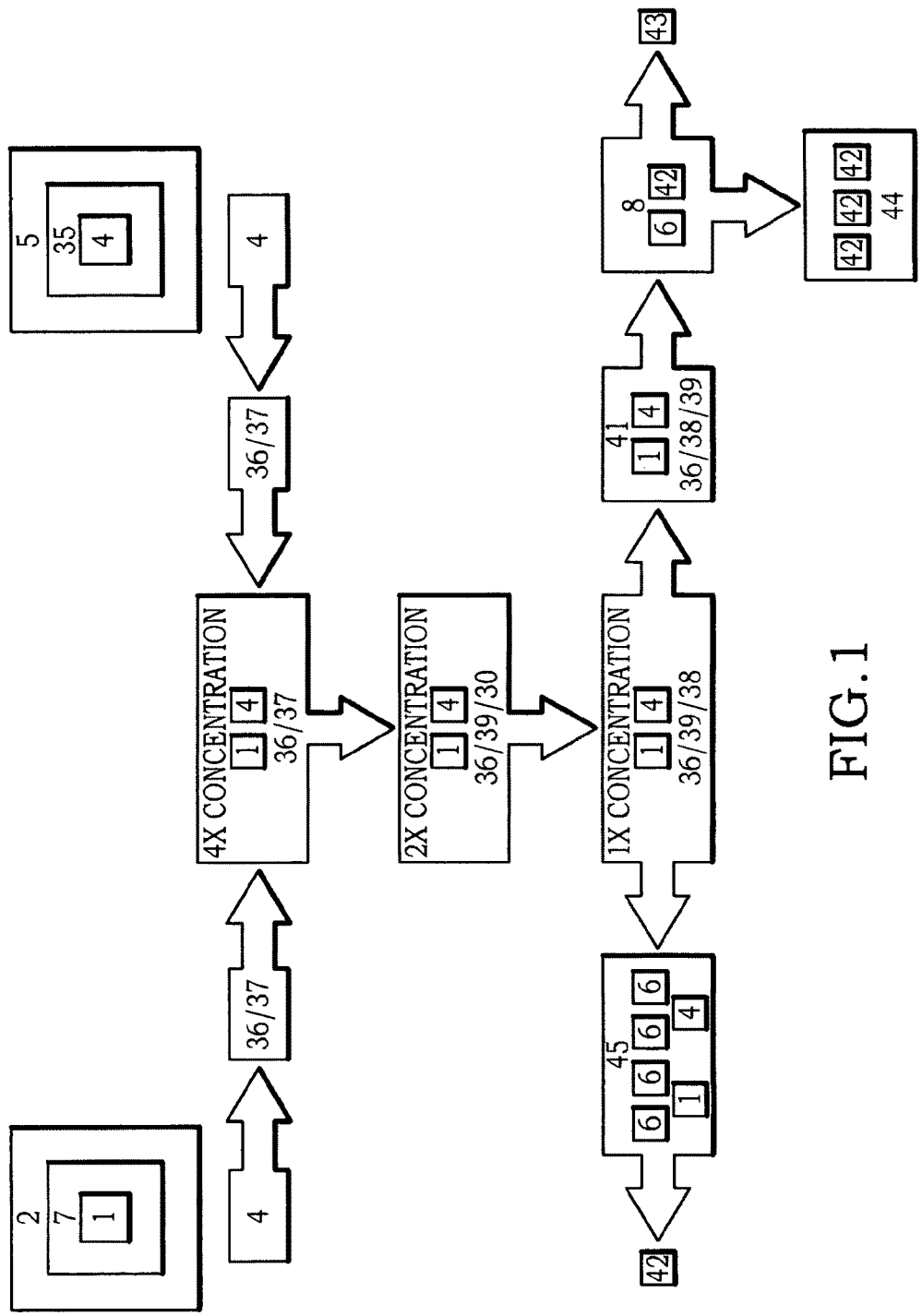
FIG. 1 is a block diagram which shows how to make and use particular embodiments of the inventive reduced dose inseminate.

Now referring to primarily to FIG. 1, fertilization efficiency of a plurality of paternal sperm cells (1) obtained from a paternal animal (2) used in a reduced dose inseminate (3) can be increased when supplemented with a plurality of heterogeneous sperm cells (4) obtained from a heterogeneous animal (5). The reduced dose inseminate (3) supplemented with a plurality of heterogeneous sperm cells (4) can perform as well as a conventional dose inseminate which contains a substantially greater amount of paternal semen (7) or a greater number of the plurality of paternal sperm cells (1).

For the purposes of this invention, the term "paternal animal" means a male animal from which an amount of paternal semen (7) can be obtained. Without limitation to the forgoing, the male animal can be a male mammal being a species of: horse, cattle, camel, deer, pig, sheep, goat, dog, cat, lion, whale, dolphin, porpoise, seal, hare, rabbit, elephant, mouse, rat, or other male mammal from which the amount of paternal semen (7) can be obtained by collection. However, as to certain embodiments of the invention, the paternal animal (2) can also be a male fish and without limiting the forgoing can be a species: salmon, tuna, sturgeon, halibut, catfish, or other male fish from which an amount of paternal semen (7) can be obtained by collection. As to other certain embodiments of the invention the paternal animal (2) can be a male bird and without limiting the forgoing can be a species: chicken, turkey, eagle, falcon, ostrich, emu, duck, goose, or other male bird from which an amount of paternal semen (7) can be collected.

For the purposes of this invention, the term "paternal semen" refers to seminal fluid which contains a plurality of paternal sperm cells (1) (sperm cells are also commonly referred to as "spermatozoa") capable of fertilizing an egg (6) (an egg is also commonly referred to as an "ovum") obtained from a female of the same species (8) as the paternal animal (1). The amount of paternal semen (7) can be obtained from the paternal animal (1) by any means which produces a sufficient plurality of paternal sperm cells (1) for use in a reduced dose inseminate (3). By way of example, and without limiting the forgoing, the amount of paternal semen (7) can be collected from a paternal animal (2) by a variety of methods such as use of an artificial vagina, manual manipulation of the penis, electrical manipulation of the anus, or the like.

For the purposes of this invention, the term "paternal sperm cells" refers to the sperm cells contained in the amount of paternal semen (7) obtained from the paternal animal (2).

For the purposes of this invention, the term "sex-selected paternal sperm cells" refers to a plurality of paternal sperm cells (1) of an amount of paternal semen (7) obtained from a paternal animal (2) which have been separated into an X-chromosome bearing population (9) and a Y-chromosome bearing population (10). Any manner or method by which the X-chromosome bearing sperm cells (11) can be separated or sorted from the Y-chromosome bearing sperm cells (12) of an amount of paternal semen (2) to provide viable sex-selected paternal sperm cells (13) for use in the reduced dose inseminate (3) can be suitable for use.

Figure 2:
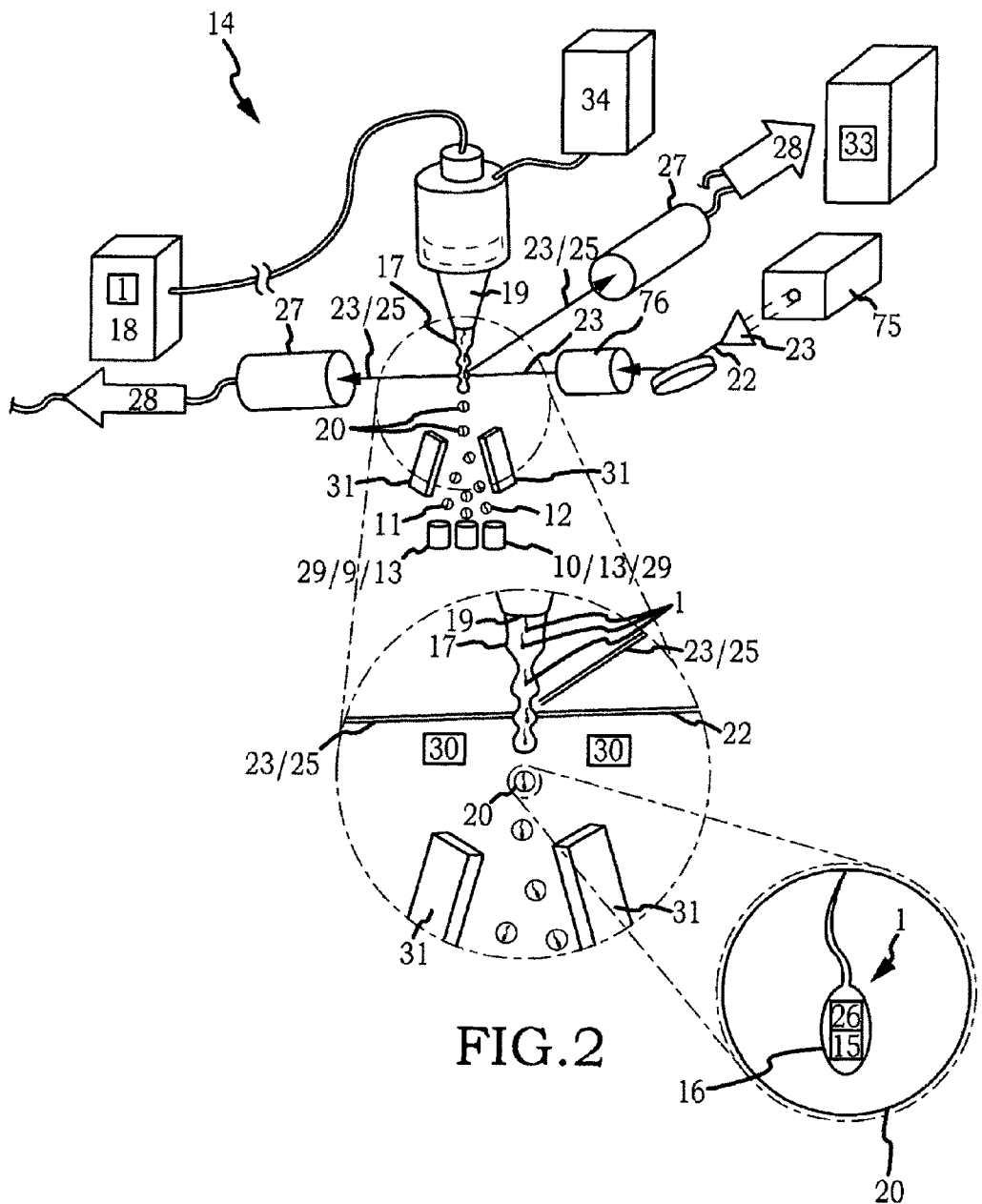
FIG. 2 is an illustration which shows a particular method of how to obtain sex-selected sperm cells of a paternal animal by use of flow cytometry.

Now referring to FIG. 2, without limiting the forgoing, X-chromosome bearing sperm cells (11) can be separated or isolated from Y-chromosome bearing sperm cells (13) of the amount of paternal semen (7) using a flow cytometer (14). The flow cytometer (14) can be configured to differentiate and sort the plurality of paternal sperm cells (1) based on the amount of deoxyribonucleic acid ("DNA") (15) within the sperm head (16). Typically, a sheath fluid source (34) delivers a fluid stream (17) in which to entrain the plurality of paternal sperm cells (1) delivered from a sperm cell source (18). The fluid stream (17) having a plurality of paternal sperm cells (1) entrained can be oscillated by a nozzle (19) to generate a plurality of droplets (20) below the nozzle (19). Each of the plurality of droplets (20) can entrain one of the plurality of paternal sperm cells (1). An illumination source (21), such as a laser, can emit a beam of light (22), or a plurality of beams of light can be generated by utilizing a beam splitting element (23) (the beam splitting element shown but not the plurality of beams of light) (or by utilizing a plurality of illumination sources (21)), which can be focused incident upon the plurality of paternal sperm cells (1) entrained in the fluid stream (17) below the nozzle (19) through an optical element (24), either as a single beam of light (22) or a plurality of beams of light, whether at the same or different wave lengths. Characteristics of the beam of light (22) can be altered by incidence upon each one of the plurality of paternal sperm cells (1) within the fluid stream (17), or an emission (25) can be generated by incidence of the beam of light (22) upon ligands (26), fluorescent materials, or the like, bound to the DNA (15) of each one of the plurality of paternal sperm cells (1). The beam(s) of light (22) having altered characteristics or the emission (25) can be received by a single or a plurality of detectors (27) which can generate a signal (28) for analysis by a computer implemented program (33) to differentiate each one of the plurality of paternal sperm cells (1) correspondingly entrained in each one of the plurality of droplets (20) based upon one or a plurality of sperm cell characteristics. Each differentiated one of the plurality of paternal sperm cells (1) can be separated based upon the presence or absence of one or a plurality of the analyzed sperm cell characteristics collected in a corresponding one of a plurality of collection elements (29). The flow cytometer (14) can further include a droplet charge generator (30) which induces a positive or negative charge in each one of the plurality of droplets (20) and a droplet deflector (31) which acts upon each one of the charged plurality of droplets (20) to establish a trajectory to the proper one of the plurality of collection elements (29). Each of the plurality of collection elements (29) thereby contains a population of the plurality of paternal sperm cells (1) which can be predominantly X-chromosome bearing sperm cells (11) or Y-chromosome bearing sperm cells (12).

The purity of the X-chromosome bearing population (9) or the Y-chromosome bearing population (10) can exceed 80% or 90% or can be of even greater purity depending upon the parameters of operating the flow cytometer (14); however, the purity level can be adjusted to be a greater or a lesser percent purity consistent with any particular application. Non-limiting examples of conventional methods of using a flow cytometer (14) to sort the plurality of paternal sperm cells (1) suitable for use in the production of a reduced dose inseminate (2) are described in U.S. Pat. Nos. 5,135,759; 6,372,422; 7,195,920 and 7,169,548, each hereby incorporated by reference in the entirety herein.

Figure 3:
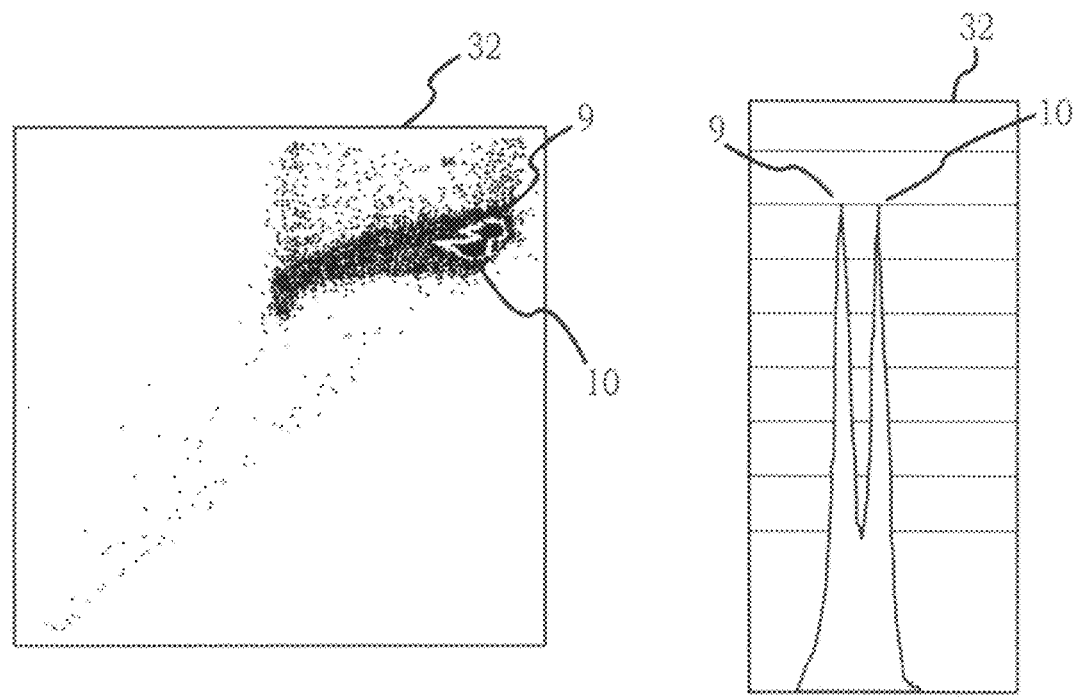
FIG. 3 is an illustration which shows a bivariate plot of paternal sperm cells separated into an X-chromosome bearing population and a Y-chromosome bearing population using a flow cytometer.

Now referring primarily to FIG. 3, a bivariate plot (32) can be generated during the use of a flow cytometer (14) to separate or sort a plurality of paternal sperm cells (1) into an X-chromosome bearing population (9) and Y-chromosome bearing population (10) as above-described is shown. The bivariate plot (32) shows that a mixture of X-chromosome bearing sperm cells (11) and Y-chromosome bearing sperm cells (12) in an amount of paternal semen (7) can be resolved into an X-chromosome bearing population (9) and a Y-chromosome bearing population (10) of paternal sperm cells (1).

As a non-limiting example, paternal semen (7) containing paternal sperm cells (1) can be obtained as an ejaculate from a paternal animal (2) such as bovine semen from a bovine animal. The bovine semen can be filtered through a filter having 80 μm pores to remove unwanted material. The bovine semen can contain about 800 million bovine sperm cells per mL to about a billion bovine sperm cells per mL with a motility of about 85%. The bovine sperm cells can be diluted by addition of TALP medium (tyrode albumin lactate pyruvate) to achieve a concentration of 100 million bovine sperm cells per mL. The bovine sperm cells can be stained by addition of about 10 μL of 15 mg/mL Hoechst 333432 to an aliquot of 4 mL of the extended bovine semen and then incubated at about 24° C. in a water bath for about 20 minutes. Addition of 2.5% (v/v) red food coloring to the stained bovine sperm cells allows dead bovine sperm cells to be differentiated and sorted away from live stained bovine sperm cells during subsequent flow cytometry procedures.

The bovine semen solution containing bovine sperm cells stained with Hoechst 333432 can be separated into enriched populations of X-chromosome bearing and Y-chromosome bearing sperm cells using as a non-limiting example a Beckman Coulter (formerly DakoCytomation or Cytomation) MOFLO SX or MOFLO XDP flowcytometer. The event rate (the number of stained sperm cells interrogated by the laser beam per second) can be adjusted at about 20,000 events per second and the sort rate (the number of stained sperm cells collected into each of the X-chromosome bearing or Y-chromosome bearing populations per second) can be adjusted in a range of about 4,500 sorts per second to about 7,000 sorts per second to collect separate X-chromosome bearing and Y-chromosome bearing populations. The sorted X-chromosome bearing and Y-chromosome bearing bovine sperm cells can be collected in TRIS A2 extender (described below). Collected X-chromosome bearing and Y-chromosome bearing populations are transferred to a cold room at about 4° C. for about 90 minutes and thereafter centrifuged to pellet the bovine sperm cells and the supernatant can be decanted. The pellet of bovine sperm cells can be resuspended in TRIS A2 to achieve a concentration of sorted or sex-selected bovine sperm cells in the range of about 8 million to about 16 million.

For the purposes of this invention, the term "heterogeneous animal" refers to an animal which is not of the same species as the paternal animal (2). As one example, the paternal animal (2) can be a bovine animal and the heterogeneous animal (5) can be any other species of animal. In certain instances, the heterogeneous animal (5) could be an animal of the same species as the paternal animal (2) but whose sperm cells are incapable of fertilizing the egg (6) of a female animal the same species (8) as the paternal animal (2). For example, a bovine male animal (or individual of other species of animal) with a genetic deficiency in sperm production which produces sperm cells which are motile but incapable of fertilizing an egg (6) the non-fertile sperm cells can be combined with the fertile plurality of sperm cells (1) of the paternal animal (2) as the heterogeneous sperm cells (4).

For the purposes of this invention the term "heterogeneous semen" refers to seminal fluid which contains a plurality of heterogeneous sperm cells (4) which are not capable of fertilizing an egg (6) obtained from a female of the same species (8) as the paternal animal (2). An amount of heterogeneous semen (35) can be obtained from a heterogeneous animal (5) by any means which produces a sufficient plurality of heterogeneous sperm cells (4) for use in a reduced dose inseminate (3). By way of example, and without limiting the forgoing, an amount of heterogeneous semen (35) can be collected from a heterogeneous animal (5) by a variety of methods such use of an artificial vagina, manual manipulation of the penis, electrical manipulation of the anus, or the like.

For the purposes of this invention, the term "heterogeneous sperm cells" refers to sperm cells contained in an amount of heterogeneous semen (35). For clarity purposes, a plurality of heterogeneous sperm cells (4) are sufficiently different from the plurality of paternal sperm cells (1) such that an egg (6) obtained from a female animal of the same species (8) as the paternal animal (2) cannot be fertilized by the plurality of heterogeneous sperm cells (4); however, the term is not intended to infer or relate to differences between individual sperm cells in the heterogeneous semen (35).

For the purposes of this invention, the term "extender" refers to a solution that comes in contact with the plurality of paternal sperm cells (1) or the plurality of heterogeneous sperm cells (4), whether as isolated populations or combined in the reduced dose inseminate (3), typically for the purpose of dilution or as a cryoprotectant. Typical examples of an extender (36) can contain one or more of: sodium citrate, Tris[hydroxymethyl]aminomethane (also referred to as "TRIS"), TES (N-Tris [Hydroxymethyl]methyl-2-aminoethanesulfonic acid), monosodium glutamate, HEPES medium such as HEPES buffered medium, HEPES buffered bovine gamete medium and particularly HBGM3 and can further contain cryoprotectants such as glycerol, dimethyl sulfoxide, ethylene glycol, propylene glycol; other organic substances such as egg yolk, an egg yolk extract, milk, a milk extract, casein, albumin, lecithin, bovine serum albumin, cholesterol; sugars such as the monosacharides, glucose, fructose, or mannose; detergents such as sodium dodecyl sulfate; antioxidants such butylated hydroxytoluene; capacitation facilitators such as alpha amylase, beta amylase, or beta glucuronidase; antibiotics such as tylosin, gentamicin, lincomycin, spectinomycin, linco-spectin (a combination of lincomycin and spectinomycin), penicillin, streptomycin, and ticarcillin; flow cytometer sheath fluids; and specifically without limiting the forgoing the particular extenders (36) referred to below as TRIS-A (37) and TRIS-B (38); although the inventive reduced dose inseminate (3) or methods of using a reduced dose inseminate (3) are not limited by the working examples which use TRIS-A as an extender (36) to dilute concentration of the plurality of paternal sperm cells (1) and the plurality of the homogeneous sperm cells (4) or which use TRIS-B (38) as a cryoprotectant (39).

For the purposes of this invention the term "TRIS-A" refers to an extender (36) having the formulation in Table 1.

TABLE 1

| TRIS-A Extender. | |
|---|---|
| TRIS | 200 mM |
| Citric Acid | 65 mM |
| Fructose | 56 mM |
| Egg Yolk* | 20% by volume |
| Water (deionized) | volume to produce formula ratio |
| Hydrochloric Acid addition to pH 6.8 | |

*Egg Yolk can be clarified by winterization process to remove certain particulates and fats.

The formulation of TRIS-A set out in Table 1 can from application to application of the invention be modified to increase viability or reduce damage to the plurality of paternal sperm cells (1) or the plurality of the homogeneous sperm cells (4) and the above formulation is provided as a non-limiting example of a numerous and wide variety of similar extenders which are suitable for use in making or using the reduced dose inseminate (3). See also, Yassen, A. M. and Foote, R. H., *Freezability of Bovine Spermatozoa in Tris-Buffered Yolk Extenders Containing Different Levels of Tris, Sodium, Potassium and Calcium Ions*, J. Dairy Science, Vol. 50, No. 6, 887-892 (1966), hereby incorporated by reference in the entirety herein. Extenders (36) in general and specifically the particular extender TRIS-A (37) can further include one or more antibiotics (40) as above described or consistent with animal health regulations of any particular jurisdiction. Also, the description of TRIS-A is not intended to limiting with respect to the wide variety of extenders (36) which can be utilized in making and using certain embodiments of the reduce dose inseminate (3) as described above.

For the purposes of this invention the term "TRIS-B" refers to an extender having the formulation in Table 2.

TABLE 2

| TRIS | 200 mM |
|---|---|
| Citric Acid | 65 mM |
| Fructose | 56 mM |
| Egg Yolk* | 20% by volume |
| Glycerol | 12%-20% by volume |
| Water (deionized) | volume to produce formula ratio |
| Hydrochloric Acid addition to pH 6.8 | |

*Egg Yolk can be clarified by winterization process to remove certain particulates and fats.

The formulation of TRIS-B set out in Table 2 can from application to application of the invention be modified to increase viability or reduce damage to the plurality of paternal sperm cells (1) or the plurality of the homogeneous sperm cells (4) and the above formulation is provided as a non-limiting example of a numerous and wide variety of similar extenders which are suitable for use in making or using the reduced dose inseminate (3). Again see for example, Yassen, A. M. and Foote, R. H., *Freezability of Bovine Spermatozoa in Tris-Buffered Yolk Extenders Containing Different Levels of Tris, Sodium, Potassium and Calcium Ions*, J. Dairy Science, Vol. 50, No. 6, 887-892 (1966). Extenders (36) in general and specifically the particualar extender TRIS-B (38) can further include one or more antibiotics (40) as above described or consistent with animal health regulations of any particular jurisdiction. Additionally, while TRIS-B (38) of the particular formulation set out in Table 2 uses glycerol as a cryoprotectant (39) the invention is not so limited. Also, the description of TRIS-B is not intended to limiting with respect to the wide variety of extenders (36) which can be utilized in making and using certain embodiments of the reduce dose inseminate (3) as described above.

An alternative formulation "TRIS-A2" refers to an extender having the formulation in Table 3.

TABLE 3

| TRIS | 297.1 mM |
|---|---|
| Citric Acid | 95.1 mM |
| Fructose | 70.2 mM |
| Egg Yolk* | 20% by volume |
| Water (deionized) | volume to produce formula ratio |
| Hydrochloric Acid addition to pH 6.8 | |

*Egg Yolk can be clarified by winterization process to remove certain particulates and fats.

The formulation of TRIS-A2 set out in Table 3 provides an example of an extender which can allow for reduced loss of sperm cell function as assessed by increased post thaw motility and duration of survival as described in greater detail below. The various formulations of TRIS A, TRIS A2, or the like being included in any reference to TRIS A unless otherwise expressly indicated.

An alternative formulation "TRIS-B2" refers to an extender having the formulation in Table 4.

TABLE 4

| TRIS | 297.1 mM |
|---|---|
| Citric Acid | 95.1 mM |
| Fructose | 70.2 mM |
| Egg Yolk* | 20% by volume |
| Glycerol | 12%-20% by volume |
| Water (deionized) | volume to produce formula ratio |
| Hydrochloric Acid addition to pH 6.8 | |

*Egg Yolk can be clarified by winterization process to remove certain particulates and fats.

The formulation of TRIS-B2 set out in Table 4 provides an example of an extender which can allow for reduced loss of sperm cell function as assessed by increased post thaw motility and duration of survival as described in greater detail below. In particular TRIS-B2 can unexpectedly reduce loss of sperm cell function as to bovine sperm cells in comparison with conventional solutions for freezing bovine sperm cells. The various formulations of TRIS B, TRIS B2, or the like being included in any reference to TRIS B unless otherwise expressly indicated.

Again referring primarily to FIG. 1, for the purpose of this invention the term "reduced dose inseminate" refers to a plurality of paternal sperm cells (1) combined with a plurality of heterogeneous sperm cells (4) without limitation to any particular dosage form (41). As to particular embodiments, the plurality of paternal sperm cells (1) and the plurality of heterogeneous sperm cells (4) can be contained in a corresponding amount of paternal semen (7) and heterogeneous semen (35) which may be diluted with an extender (36) (such as TRIS A, TRIS A2, TRIS B, TRIS B2) prior to, as part of a procedure resulting in the combination, or after combination. As to other particular embodiments, the plurality of paternal sperm cells (1) can be sex-selected paternal sperm cells (13) to provide an X-chromosome bearing population (9) or a Y-chromosome bearing population (10) which can be combined with the plurality of heterogeneous sperm cells (4). As to yet other particular embodiments, the reduced dose inseminate (3) may be an amount by volume of the combination of the plurality of paternal cells (1) (whether or not sex-selected paternal sperm cells (13)) and the heterogeneous sperm cells (4) along with an amount of an extender (36). The volume of the combination of paternal sperm cells (1) and heterogeneous sperm cells (4) and the concentration or the ratio of the paternal sperm cells (1) and heterogeneous sperm cells (4) within a volume can vary depending on the application. Other particular embodiments of the reduced dose inseminate (3) can further include a particular dosage form (41). As one non-limiting example, the dosage form (41) for artificial insemination of cattle can be a one-quarter cubic centimeter (0.25 mL) artificial insemination straw which contains the reduced dose inseminate (3). As to certain embodiments of the reduced dose inseminate (3), the combination of paternal sperm cells (1) and heterogeneous sperm cells (4), can otherwise be produced by the steps or procedures as any particular conventional insemination dose, however, the resulting reduced dose inseminate (3) can by comparison contain fewer paternal sperm cells (1) (hence a reduced dose or low dose of paternal sperm cells (1)) capable of fertilizing an egg (6) of a female of the same species as the paternal animal (2).

As a general non-limiting example, a reduced dose inseminate (3) which contains a reduced dose (or low dose) of paternal sperm cells (1) can be made by obtaining an amount of paternal semen (7) or an amount of sex-selected paternal sperm cells (13) (as to each fresh or cryopreserved) of a paternal animal (2) such as a bull, stallion, ram, bill goat, boar, or otherwise. The amount of paternal semen (7) or sex-selected paternal sperm cells (13) can be extended with TRIS-A (38) extender (or other extender (36)) to achieve a concentration of the extended plurality of paternal sperm cells (1) of about four times greater than the concentration of the plurality of paternal sperm cells (1) in the particular embodiment of the reduced dose inseminate (3) to be produced. Embodiments of the reduced dose inseminate (3) will typically have a concentration of the plurality of paternal sperm cells (1) in a range of about 200,000 paternal sperm cells (1) per milliliter and about 40 million paternal sperm cells (1) per milliliter depending upon various factors such as the species of the paternal animal (2), the scarcity of the paternal semen (7), the fertility of the paternal semen (7), the dosage form (41), the method of insemination (whether artificial insemination or in vitro fertilization), whether for multiple ovulation embryo transfer or single ovulation single embryo production, the female animal of the same species as the paternal animal (2) being inseminated, or the like. Accordingly, the four times concentration of the paternal sperm cells (1) in TRIS-A (37) (TRIS A2 or other extender) can be in a range of about 800,000 paternal sperm cells (1) per milliliter and about 160 million paternal sperm cells (1) per milliliter of TRIS-A (37) (TRIS A2 or other extender).

The extended paternal semen (7) or sex-selected paternal sperm cells (13) can be cooled to a temperature in a range of about 4 degrees Celsius ("° C.") and about 5° C. The cooled extended paternal semen (7) or sex-selected paternal sperm cells (13) can be held at this temperature to allow the membranes of the paternal sperm cells (1) to move toward equilibrium or equilibrate with the TRIS-A (typically a period of about 90 minutes or as to certain embodiments not less than 90 minutes). The cooled extended paternal sperm cells (7) can be held in this condition not to exceed a length of time in which the paternal sperm cells (7) remain viable or capable fertilizing an egg (6) of a female of the same species (8) as the paternal animal (2). Typically, the period of time held will not exceed 12 hours.

An amount of heterogeneous semen (35) can be obtained from a heterogeneous animal (5) (or as cryopreserved heterogeneous semen (35) of the heterogeneous animal (5)). The heterogeneous semen (35) can be suspended in an amount of TRIS-A (37) (or other extender (36)) and then centrifuged in range of about 500 rounds per minute ("rpm") and about 5,000 rpm for a period in a range of between about one minute and about ten minutes. The supernatant can be decanted and the pellet containing the plurality of heterogeneous sperm cells (4) can be suspended in an amount of TRIS-A (37) to achieve a concentration of the plurality of heterogeneous sperm cells (4) of about four times greater than the concentration of the plurality of heterogeneous sperm cells (4) in the particular embodiment of the reduced dose inseminate (3) to be produced. Embodiments of the reduced dose inseminate (3) will typically have a concentration of the plurality of heterogeneous sperm cells (4) in a range of about 4 million heterogeneous sperm cells (4) per milliliter and about 80 million heterogeneous sperm cells (4) per milliliter depending upon various factors above described with regard to the paternal sperm cells (1) and the efficiency of the particular heterogeneous sperm cells (4) to enhance characteristics of the paternal sperm cells (1) such as viability, motility, fertility, or the like. Accordingly, four times concentration of the plurality of heterogeneous sperm cells (1) in TRIS-A (37) (or other extender (36)) can be in a range of about 16 million heterogeneous sperm cells (4) per milliliter and about 320 million heterogeneous sperm cells (1) per milliliter of TRIS-A (37).

The extended heterogeneous sperm cells (4) can be cooled to a temperature in a range of about 4° C. and about 5° C. The cooled extended heterogeneous sperm cells (4) can be held at this temperature to allow the membranes of the hetergenous sperm cells (4) to move toward equilibrium or equilibrate with the TRIS-A (typically a period of about 90 minutes or as to certain embodiments not less than 90 minutes). The cooled extended heterogeneous sperm cells (4) can be held in this condition until combined with the paternal sperm cells (4).

About equal volumes of the cooled extended paternal sperm cells (1) or sex-selected paternal sperm cells (13) and the cooled extended heterogeneous sperm cells (4) can be combined to achieve two times greater concentration of each of the paternal sperm cells (1) or the heterogeneous sperm cells (4) with respect to the final concentration of each in the reduced dose inseminate (3) to be produced.

To the two fold concentrated combination of the plurality of paternal sperm cells (1) and heterogeneous sperm cells (4), about an equal volume of TRIS-B (38) (or TRIS B2 containing between about 12% and 20% glycerol) (or other similar extender) can be added and the mixture can be cooled to temperature in a range of about 4° C. and about 5° C. The cooled extended combination of paternal sperm cells (1) and heterogeneous sperm cells (4) can be held at this temperature to allow the membranes of the paternal sperm cells (1) and the heterogeneous sperm cells (4) to move toward equilibrium or equilibrate with the TRIS-B (typically a period in the range of about 30 minutes and about 90 minutes or as to certain embodiments not less than 90 minutes). The cooled extended combination of paternal sperm cells (7) and heterogeneous sperm cells (4) can be held in this condition not to exceed a length of time in which the paternal sperm cells (1) remain viable or capable fertilizing an egg (6) of a female of the same species as the paternal animal (2).

The cooled extended combination of paternal sperm cells (1) and heterogeneous sperm cells (4) can be handled by normal procedures utilized for producing doses of the paternal semen (7). Accordingly, as to certain embodiments, the cooled extended combination of paternal sperm cells (1) and heterogeneous sperm cells (4) can be aliquoted into 0.25 mL artificial insemination straws. The reduced dose inseminate (3) of this dosage form (41) (0.25 mL artificial insemination straw) provides a plurality of paternal sperm cells (1) typically in the range of about 50,000 and about 10 million and a plurality of heterogeneous sperm cells (4) in the range of about 1 million and about 20 million. However, a greater or lesser number of paternal sperm cells (1) can be included in the reduced dose inseminate (3) depending on the scarcity or viability of the paternal semen (7) or sex-selected paternal sperm cells (13).

The reduced dose inseminate (3) can used for artificial insemination to fertilize the egg(s) (6) of a female of the same species (8) as the paternal animal (2) to for the production of embryos (42) whether as single embryo pregnancies to generate offspring (43) for meat or animal replacement or multiple embryo pregnancies for multiple ovulation embryo production and subsequent flushing of multiple embryos (44). Pregnancy rates resulting from the use of the inventive reduced dose inseminate (3) can be at the same level as when conventional dose inseminates are utilized in artificial insemination procedures.

Alternately, the reduced dose inseminate (3) can be used in vitro fertilization (45) procedures to fertilize eggs (6) of obtained from a female animal of the same species (8) to produce in vitro fertilized embryos (42).

A particular non-limiting example of a reduced dose inseminate (3) can be prepared by obtaining one milliliter of fresh paternal semen (7) from a bull of a bovine species of a dairy or beef breed (the paternal animal (2)). The one milliliter of fresh paternal semen (7) of a bull of a bovine species will typically contain about one billion paternal sperm cells (1) which can be extended with TRIS-A (37) to achieve a concentration of paternal sperm cells (1) of about 16 million per milliliter ("mL") in final volume of about 62.6 mL. The extended paternal semen (7) can be cooled to temperature in a range of about 4° C. and about 5° C. and held for period of about 90 minutes.

Twenty-five milliliters of fresh heterogeneous semen (35) can be obtained from a bill goat(s), each milliliter containing about one billion heterogeneous sperm cells (4), can be centrifuged at about 2000 rpm for about 5 minutes. The supernatant can be discarded and the heterogeneous sperm cells (4) extended with TRIS-A (37) to a concentration of heterogeneous sperm cells (4) of about 320 million per milliliter with a final volume of about 69.4 mL. The extended heterogeneous sperm cells (4) can be cooled to a temperature in a range of about 4° C. and about 5° C. and held for period of about 90 minutes.

About equal volumes of the cooled extended paternal sperm cells (1) and cooled extended heterogeneous sperm cells (4) (about 60 mL cooled extended bull semen about 16 million sperm cells per mL and about 60 mL cooled extended bill goat semen about 320 million sperm cells per mL) can be combined and extended to a total volume of about 240 mL with TRIS-B (38). The extended combination of paternal sperm cells (1) and heterogeneous sperm cells (4) can be cooled to a temperature in a range of about 4° C. and about 5° C. and held for period of about 30 minutes.

The cooled extended combination of paternal sperm cells (1) of a bovine bull and heterogeneous sperm cells (4) of a bill goat(s) at 4° C. can be aliquoted into a plurality of 0.25 mL artificial insemination straws (about 960 0.25 mL artificial insemination straws can be produced from the total volume of 240 mL) to produce a corresponding plurality of reduced dose inseminate (3) in the dosage form of a 0.25 mL artificial insemination straws. Each of the plurality of reduced dose inseminate (3) contain about one million paternal sperm cells (1) of a bovine bull and about 20 million heterogeneous sperm cells (4) of the bill goat(s). The plurality of reduced dose inseminate (3) were frozen by conventional cryopreservation procedures.

Artificial insemination using a single frozen-thawed reduced dose inseminate (3) in a single estrous cycle in the dosage form of a 0.25 mL artificial insemination straw produced as above described were used to artificially inseminate 118 female bovine animals of the species (8) of the paternal animal (2) (118 cows) by otherwise conventional artificial insemination procedures resulting in 66 pregnancies (56% pregnancy rate). These results show that use of the inventive reduced dose inseminate (3) in conventional artificial insemination procedures can achieve pregnancy rates comparable to the use of a normal dose inseminate (a normal dose inseminate can contain about 20 million paternal sperm cells of a bull of a bovine species) in control groups in which a pregnancy rate of between about 50% and about 65% can be achieved.

A second particular non-limiting example of a reduced dose inseminate (3) can be prepared by obtaining one milliliter of fresh paternal semen (7) from a bill goat (the paternal animal (2)). The one milliliter of fresh paternal semen (7) of the bill goat will typically contain about one billion paternal sperm cells (1) which can be extended with TRIS-A (37) to achieve a concentration of paternal sperm cells (1) of about 32 million per milliliter ("mL") in final volume of about 31.3 mL. The extended paternal semen (7) can be cooled to temperature in a range of about 4° C. and about 5° C. and held for period of about 90 minutes.

Fifteen milliliters of fresh heterogeneous semen (35) can be obtained from a ram(s), each milliliter containing about one billion heterogeneous sperm cells (4), can be centrifuged at about 2000 rpm for about 5 minutes. The supernatant can be discarded and the heterogeneous sperm cells (4) extended with TRIS-A (37) to a concentration of heterogeneous sperm cells (4) of about 320 million per milliliter with a final volume of about 46.9 mL. The extended heterogeneous sperm cells (4) can be cooled to a temperature in a range of about 4° C. and about 5° C. and held for period of about 90 minutes.

About equal volumes of the cooled extended paternal sperm cells (1) and cooled extended heterogeneous sperm cells (4) (about 30 mL cooled extended bill goat semen about 32 million sperm cells per mL and about 30 mL cooled extended ram semen about 320 million sperm cells per mL) can be combined and extended to a total volume of about 120 mL with TRIS-B (38). The extended combination of paternal sperm cells (1) and heterogeneous sperm cells (4) can be cooled to a temperature in a range of about 4° C. and about 5° C. and held for period of about 30 minutes.

The cooled extended combination of paternal sperm cells (1) of a bill goat and heterogeneous sperm cells (4) of a ram(s) at 4° C. can be aliquoted into a plurality of 0.25 mL artificial insemination straws (about 480 0.25 mL artificial insemination straws can be produced from the total volume of 120 mL) to produce a corresponding plurality of reduced dose inseminate (3) in the dosage form of a 0.25 mL artificial insemination straws. Each of the plurality of reduced dose inseminate (3) contain about two million paternal sperm cells (1) of a bill goat and about 20 million heterogeneous sperm cells (4) of the ram. The plurality of reduced dose inseminate (3) were frozen by conventional cryopreservation procedures.

Artificial insemination by laproscopic uterus insemination using a single frozen-thawed reduced dose inseminate (3) in a single estrous cycle in the dosage form of a 0.25 mL artificial insemination straw produced as above described for 125 female goat cows by otherwise conventional artificial insemination by laproscopic uterus insemination procedures resulting in 64 pregnancies (51% pregnancy rate). These results show that use of the inventive reduced dose inseminate (3) can achieve pregnancy rates comparable to the use of a normal dose inseminate (a normal dose inseminate can contain about 20 million paternal sperm cells of a bill goat).

As third particular non-limiting example of a reduced dose inseminate (3) can include an amount of heterogeneous semen (35) containing heterogeneous sperm cells (4) obtained from a bill goat (1 billion to 1.5 billion sperm cells per mL). The fresh bill goat semen can be mixed 1:1 with TRIS A2. The mixture can be filtered through a filter having 80 μm pores to remove unwanted material. TRIS A2 can be added to achieve a concentration of bill goat sperm cells in the range of about 32 million per mL to about 48 million per mL. The extended bill goat semen can be stored at about 4° C. for a period in the range of about 10 hours to about 12 hours.

Enriched populations of X-chromosome bearing or Y-chromosome bearing bovine sperm cells (paternal sperm cells (1)) obtained by flow cytometery, as above described (or other separation methods) can be combined with the bill goat semen prepared as above described to achieve a final concentration of X-chromosome bearing bovine sperm cells or Y-chromosome bearing bovine sperm cells in the range of about 4 million and about 8 million (the concentration of X-chromosome bearing or Y-chromosome bearing sperm cells may contain a certain percentage of the other sex of sperm cell) and a concentration of bill goat sperm cells in the range of about 16 million per mL and about 24 million per mL.

The combination of the paternal sperm cells (1) (X-chromosome bearing or Y-chromosome bearing bovine sperm cells obtained by a method of separation) and the heterogeneous sperm cells (4) (bill goat sperm cells) can be then be immediately mixed with TRIS B2 to achieve a final concentration of the X-chromosome bearing or Y-chromosome bearing bovine sperm cells in the range of about 2 million per mL to about 4 million per mL and a final concentration of the bill goat sperm cells in the range of about 8 million per mL to about 12 million per mL. The resulting particular embodiment of a reduced dose inseminate (3) then held at about 4° C. for about 30 minutes.

The equilibrated reduced dose inseminate (3) can then be transferred into 0.25 mL artificial insemination straws at about 4° C. Each 0.25 mL artificial insemination straw containing X-chromosome bearing or Y-chromosome bearing bovine sperm cells in the range of about 500,000 to about 1 million and bill goat sperm cells in the range of about 2 million to about 3 million.

The artificial insemination straws containing the combination of paternal sperm cells (1) and heterogeneous sperm cells (4) (reduced dose inseminate (3)) prepared as above described can be placed into freezing unit to bring the temperature proximate −96° C., then the artificial insemination straws containing the reduced dose inseminate (3) can be placed into liquid nitrogen to further reduce the temperature proximate −120° C. The artificial insemination straws containing the reduced dose inseminate (3) can then transferred to liquid nitrogen to further reduce the temperature to −196° C. for storage.

A comparison of frozen thawed reduced dose inseminate (3) containing the combination of flow sorted X-chromosome bearing or Y-chromosome bearing bovine sperm cells (paternal sperm cells (1)) and bill goat sperm cells (heterogeneous sperm cells (4)) prepared as above described was compared with similarly prepared flow cytometry sorted X-chromosome bearing or Y-chromosome bearing bovine sperm cells without the addition of goat sperm cells as to 0 hour motility (motility at immediately upon thawing), acrosome intactness, and total survival time after thawing (the duration of time having an end point based on the last to die sperm cell in a sample population).

TABLE 5

Comparison of Post Thaw Motility and Survival Time Between Reduced Dose Inseminate And Flow Sorted Sperm Cells.

| Inseminate | 0 Hour Motility | Survival Time |
|---|---|---|
| Reduced Dose Inseminate[1] | 40%-60% | 8 hrs-10 hrs |
| Flow Sorted Bovine Sperm Cells[2] | 30%-40% | 4 hrs-6 hrs |

[1]Combination of flow sorted X-chromosome bearing or Y-chromosome bearing bovine sperm cells (paternal sperm cells)(0.5-1M/0.25 mL) and bill goat sperm cells (heterogeneous sperm cells)(2-3M/0.25 mL).
[2]Flow sorted X-chromosome bearing or Y-chromosome bearing bovine sperm cells (0.5-1M/0.25 mL).

Now referring to Table 5, which summarizes the results of a comparison of post thaw motility and survival time between a reduced dose inseminate (3) containing a combination of flow sorted bovine sperm cells (either X-chromosome bearing or Y-chromosome bearing sperm cells) and bill goat sperm cells prepared as above described and conventional flow cytometry sorted bovine sperm cells (either X-chromosome bearing or Y-chromosome bearing sperm cells) without combination with bill goat sperm cells, but otherwise prepared as above described, it can be understood that the reduced dose inseminate (3) has a greater 0 hour motility and greater survival time.

TABLE 6

Comparison of Artificial Insemination Using Reduced Dose Inseminate and Conventional Dose Inseminate As To Conception Nos. And Birthrate.

| Inseminate | Donor Cows | Conception (%) | Calves Born (female/male) | % Female |
|---|---|---|---|---|
| Reduced Dose Inseminate[1] | 5,335 | 3,020 (56.6) | 2,960 (2770/190) | 93.6 |
| Conventional Semen[2] | 2,246 | 1,328 (59.1) | 1,301 (664/637) | 51.0 |

[1]Combination of flow sorted X-chromosome bearing (paternal sperm cells)(0.5-1M/0.25 mL) and bill goat sperm cells (heterogeneous sperm cells)(2-3M/0.25 mL).
[2]Bovine Semen conventionally prepared (10M/0.25 mL).

Now referring to Table 6, which summarizes the results of a comparison of conception rates, ratio of female:male calves born, and % female from artificial insemination of 5,335 donor cows with a reduced dose inseminate (3) in the dosage form of a 0.25 mL artificial insemination straw containing a combination of X-chromosome bearing bovine sperm cells obtained by flow cytometery (0.5 million to about 1 million per artificial insemination straw) and bill goat sperm cells (2 million to about 3 million per artificial insemination straw) and artificial insemination of 2,246 donor cows artificially inseminated with a conventional dose inseminate in the dosage form of a 0.25 mL artificial insemination straw containing bovine semen (about 10 million per artificial insemination straw), it can be understood that the reduced dose inseminate (0.5M-1M flow cytometry sorted bovine sperm cells per dose) uses fewer paternal sperm cells (1) per dose as compared to a conventional dose of semen (10M bovine sperm cells per dose) yet achieves substantially the same or similar conception rate with the additional advantage of producing offspring of a pre-selected sex. In this particular embodiment of the invention in which the reduced dose inseminate (3) contains greater than 90% X-chromosome bearing sperm cells the percent female offspring was 93.6.

A fourth particular non-limiting example of a reduced dose inseminate (3) can include an amount of heterogeneous semen (35) containing heterogeneous sperm cells (4) obtained from a bill goat. The fresh bill goat semen can be mixed 1:1 with TRIS A2. The mixture can be filtered through a filter having 80 μm pores to remove unwanted material. The filtered bill goat semen contained about 1.48 billion bill goat sperm cells with a motility of about 85%. TRIS A2 can be added to achieve a concentration of about 32 million per mL. The extended bill goat semen can be stored at about 4° C. for a period in the range of about 10 hours to about 12 hours.

An enriched population of Y-chromosome bearing bovine sperm cells (paternal sperm cells (1)) can be combined with the bill goat semen prepared as above described to achieve a reduced dose inseminate (3) having a final concentration of Y-chromosome bearing bovine sperm cells in the range of about 8 million and a final concentration of bill goat sperm cells of about 16 million.

The combination of the paternal sperm cells (1) (Y-chromosome bearing bovine sperm cells) and the heterogeneous sperm cells (4) (bill goat sperm cells) can be then be immediately mixed with TRIS B2 to achieve a final concentration of the Y-chromosome bearing bovine sperm cells of about 4 million and a final concentration of the bill goat sperm cells of about 8 million. The resulting embodiment of a reduced dose inseminate (3) then held at about 4° C. for about 30 minutes.

The equilibrated reduced dose inseminate (3) can then be transferred into 0.25 mL artificial insemination straws at about 4° C. Each 0.25 mL artificial insemination straw containing Y-chromosome bearing bovine sperm cells of about 1 million and bill goat sperm cells of about 2 million.

The artificial insemination straws containing the combination of paternal sperm cells (1) and heterogeneous sperm cells (4) (reduced dose inseminate (3)) prepared as above described can be placed into freezing unit to bring the temperature proximate −96° C., then the artificial insemination straws containing the reduced dose inseminate (3) can be placed into liquid nitrogen to further reduce the temperature proximate −120° C. The artificial insemination straws containing the reduced dose inseminate (3) can then be transferred to liquid nitrogen to further reduce the temperature to −196° C. for storage.

A comparison of frozen thawed reduced dose inseminate (3) containing the combination of Y-chromosome bearing bovine sperm cells (paternal sperm cells (1)) and bill goat sperm cells (heterogeneous sperm cells (4)) prepared as above described was compared with similarly prepared flow sorted Y-chromosome bearing bovine sperm cells without the addition of goat sperm cells as to 0 hour motility (motility at immediately upon thawing), acrosome intactness, and total survival time after thawing (the duration of time with the end point based on the last to die sperm cell in the sample population).

TABLE 7

Comparison of Post Thaw Motility and Survival Time Between Reduced Dose Inseminate And Flow Sorted Sperm Cells.

| Inseminate | 0 Hour Motility | Survival Time |
|---|---|---|
| Reduced Dose Inseminate[1] | 60% | 10 hrs |
| Flow Sorted Bovine Sperm Cells[2] | 30%-40% | 4 hrs-6 hrs |

[1]Combination of flow sorted Y-chromosome bearing bovine sperm cells (paternal sperm cells)(1M/0.25 mL) and bill goat sperm cells (heterogeneous sperm cells)(3M/0.25 mL).
[2]Flow sorted Y-chromosome bearing bovine sperm cells (1M/0.25 mL).

Now referring to Table 7, which summarizes the results of a comparison of post thaw motility and survival time between a reduced dose inseminate (3) containing a combination of flow sorted bovine sperm cells (Y-chromosome bearing sperm cells) and bill goat sperm cells prepared as above described and conventional flow cytometry sorted bovine sperm cells (Y-chromosome bearing sperm cells) without combination with bill goat sperm cells, but otherwise prepared as above described, it can be understood that the reduced dose inseminate (3) has a greater 0 hour motility and greater survival time.

Artificial insemination of 180 donor cows with a corresponding 180 0.25 mL artificial insemination straws each containing a reduced dose inseminate prepared as above described resulted in a conception rate of 58% (105/108) from which 99 male calves were born proving a 94% purity of the Y-chromosome bearing population of bovine sperm cells achieved by flow sorting as above-described.

A fifth particular non-limiting example of a reduced dose inseminate (3) can include an amount of heterogeneous semen (35) containing heterogeneous sperm cells (4) obtained from a pig. Fifteen mL of fresh pig semen can diluted with TRIS A2 (1:1) and filtered through a filter having 80 μm pores to remove unwanted material. The filtered pig semen contained about 1.2 billion pig sperm cells per mL with a motility of about 85%. TRIS A2 can be added to achieve a concentration of about 32 million per mL. The extended pig semen can be stored at about 4° C. for a period in the range of about 10 hours to about 12 hours.

Enriched populations of X-chromosome bearing bovine sperm cells (paternal sperm cells (1)) can be combined with the pig semen prepared as above described to achieve a final concentration of X-chromosome bearing bovine sperm cells in the range of about 4 million and a concentration of pig sperm cells in the range of about 8 million per mL.

The combination of the paternal sperm cells (1) (X-chromosome bearing bovine sperm cells) and the heterogeneous sperm cells (4) (pig sperm cells) can be then be immediately mixed with TRIS B2 to achieve in the combination a final concentration of the X-chromosome bearing bovine sperm cells of about 4 million and a final concentration of the pig sperm cells of about 8 million. The resulting embodiment of a reduced dose inseminate (3) then held at about 4° C. for about 30 minutes.

The equilibrated reduced dose inseminate (3) can then be transferred into 0.25 mL artificial insemination straws at about 4° C. Each 0.25 mL artificial insemination straw can contain X-chromosome bearing bovine sperm cells of about 1 million and pig sperm cells of about 2 million.

The artificial insemination straws containing the combination of paternal sperm cells (1) and heterogeneous sperm cells (4) (reduced dose inseminate (3)) prepared as above described can be placed into freezing unit to bring the temperature proximate −96° C., then the artificial insemination straws containing the reduced dose inseminate (3) can be placed into liquid nitrogen to further reduce the temperature proximate −120° C. The artificial insemination straws containing the reduced dose inseminate (3) can then transferred to liquid nitrogen to further reduce the temperature to −196° C. for storage.

A comparison of frozen thawed reduced dose inseminate (3) containing the combination of X-chromosome bearing bovine sperm cells (paternal sperm cells (1)) and pig sperm cells (heterogeneous sperm cells (4)) prepared as above described was compared with similarly prepared flow cytometry sorted X-chromosome bearing bovine sperm cells without the addition of pig sperm cells as to 0 hour motility (motility at immediately upon thawing), acrosome intactness, and total survival time after thawing (the duration of time having an end point based on the last to die sperm cell in the sample population).

TABLE 8

Comparison of Post Thaw Motility and Survival Time Between Reduced Dose Inseminate And Flow Sorted Sperm Cells.

| Inseminate | 0 Hour Motility | Survival Time |
|---|---|---|
| Reduced Dose Inseminate[1] | 58% | 10 hrs |
| Flow Sorted Bovine Sperm Cells[2] | 30%-40% | 4 hrs-6 hrs |

[1]Combination of flow sorted X-chromosome bearing bovine sperm cells (paternal sperm cells)(1M/0.25 mL) and pig sperm cells (heterogeneous sperm cells)(2M/0.25 mL).
[2]Flow sorted Y-chromosome bearing bovine sperm cells (1M/0.25 mL).

Now referring to Table 8, which summarizes the results of a comparison of post thaw motility and survival time between a reduced dose inseminate (3) containing a combination of flow sorted bovine sperm cells (X-chromosome bearing sperm cells) and pig sperm cells prepared as above described and flow cytometry sorted bovine sperm cells (X-chromosome bearing sperm cells) without combination with pig sperm cells, but otherwise prepared as above described, it can be understood that the reduced dose inseminate (3) has a greater 0 hour motility and greater survival time.

Artificial insemination of 100 donor cows with a corresponding 100 0.25 mL artificial insemination straws each containing a reduced dose inseminate prepared as above described resulted in a conception rate of 57% (57/108) from which 54 female calves were born proving a 95% purity of the X-chromosome bearing population of bovine sperm cells achieved by flow cytometry sorting as above-described.

A sixth particular non-limiting example of a reduced dose inseminate (3) can include an amount of heterogeneous semen (35) containing heterogeneous sperm cells (4) obtained from a deer. Fresh deer semen in an amount of 2.8 mL was collected diluted with TRIS A2 (1:1) and filtered through a filter having 80 μm pores to remove unwanted material. The filtered deer semen contained about 700 million sperm cells per mL with a motility of about 90%. TRIS A2 can be added to achieve a concentration of about 32 million deer sperm cells per mL. The extended deer semen can be stored at about 4° C. for a period in the range of about 10 hours to about 12 hours.

Enriched populations of X-chromosome bearing bovine sperm cells (paternal sperm cells (1)) can be combined with the deer semen (heterogeneous sperm cells (4)) prepared as above described to achieve a final concentration of X-chromosome bearing bovine sperm cells of about 8 million and a concentration of deer sperm cells of about 16 million per mL.

The combination of the paternal sperm cells (1) (X-chromosome bearing bovine sperm cells) and the heterogeneous sperm cells (4) (deer sperm cells) can then be immediately mixed with TRIS B2 to achieve a final concentration of the X-chromosome bearing bovine sperm cells of about 4 million and a final concentration of the deer sperm cells of about 8 million. The resulting embodiment of a reduced dose inseminate (3) then held at about 4° C. for about 30 minutes.

The equilibrated reduced dose inseminate (3) can then be transferred into 0.25 mL artificial insemination straws at about 4° C. Each 0.25 mL artificial insemination straw containing X-chromosome bearing bovine sperm cells of about 1 million and deer sperm cells of about 2 million.

The artificial insemination straws containing the combination of paternal sperm cells (1) and heterogeneous sperm cells (4) (reduced dose inseminate (3)) prepared as above described can be placed into freezing unit to bring the temperature proximate −96° C., then the artificial insemination straws containing the reduced dose inseminate (3) can be placed into liquid nitrogen to further reduce the temperature proximate −120° C. The artificial insemination straws containing the reduced dose inseminate (3) can then be transferred to liquid nitrogen to further reduce the temperature to −196° C. for storage.

A comparison of frozen thawed reduced dose inseminate (3) containing the combination of X-chromosome bearing bovine sperm cells (paternal sperm cells (10) and deer sperm cells (heterogeneous sperm cells (4)) prepared as above described was compared with similarly prepared flow sorted X-chromosome bearing bovine sperm cells without the addition of deer sperm cells as to 0 hour motility (motility at immediately upon thawing), acrosome intactness, and total survival time after thawing (the duration of time based on the last to die sperm cell in a sample population).

TABLE 9

Comparison of Post Thaw Motility and Survival Time Between Reduced Dose Inseminate And Flow Sorted Sperm Cells.

| Inseminate | 0 Hour Motility | Survival Time |
|---|---|---|
| Reduced Dose Inseminate[1] | 60% | 10 hrs |
| Flow Sorted Bovine Sperm Cells[2] | 30%-40% | 4 hrs-6 hrs |

[1]Combination of flow sorted X-chromosome bearing bovine sperm cells (paternal sperm cells)(1M/0.25 mL) and deer sperm cells (heterogeneous sperm cells)(2M/0.25 mL).
[2]Flow sorted X-chromosome bearing bovine sperm cells (1M/0.25 mL).

Now referring to Table 9, which summarizes the results of a comparison of post thaw motility and survival time between a reduced dose inseminate (3) containing a combination of flow sorted bovine sperm cells (X-chromosome bearing bovine sperm cells) and deer sperm cells prepared as above described and flow cytometry sorted bovine sperm cells (X-chromosome bearing) without combination with deer sperm cells, but otherwise prepared as above described, it can be understood that the reduced dose inseminate (3) has a greater 0 hour motility and greater survival time.

Artificial insemination of 120 donor cows with a corresponding 120 0.25 mL artificial insemination straws each containing a reduced dose inseminate prepared as above described resulted in a conception rate of 63% (77/120) from which 74 female calves were born proving a 96% purity of the X-chromosome bearing population of bovine sperm cells achieved by flow cytometry sorting as above-described.

A seventh particular non-limiting example of a reduced dose inseminate (3) can include an amount of heterogeneous semen (35) containing heterogeneous sperm cells (4) obtained from a horse. Fresh horse semen in an amount of 23 mL was collected, diluted with TRIS A2 and filtered through a filter having 80 μm pores to remove unwanted material. The filtered horse semen contained about 140 million sperm cells per mL with a motility of about 850%. TRIS A2 can be added to achieve a concentration of about 32 million per mL. The extended horse semen can be stored at about 4° C. for a period in the range of about 10 hours to about 12 hours.

Enriched populations of X-chromosome bearing bovine sperm cells (paternal sperm cells (1)) can be combined with the horse semen prepared as above described to achieve a final concentration of X-chromosome bearing bovine sperm cells in the range of about 8 million and a concentration of horse sperm cells in the range of about 16 million per mL of the combination.

The combination of the paternal sperm cells (1) (X-chromosome bearing bovine sperm cells) and the heterogeneous sperm cells (4) (horse sperm cells) can be then be immediately mixed with TRIS B2 to achieve a final concentration of the X-chromosome bearing bovine sperm cells of about 4 million and a final concentration of the horse sperm cells of about 8 million. The resulting embodiment of a reduced dose inseminate (3) then held at about 4° C. for about 30 minutes.

The equilibrated reduced dose inseminate (3) can then be transferred into 0.25 mL artificial insemination straws at about 4° C. Each 0.25 mL artificial insemination straw containing X-chromosome bearing bovine sperm cells of about 1 million and horse sperm cells of about 2 million.

The artificial insemination straws containing the combination of paternal sperm cells and heterogeneous sperm cells (reduced dose inseminate (3)) prepared as above described can be placed into freezing unit to bring the temperature proximate −96° C., then the artificial insemination straws containing the reduced dose inseminate (3) can be placed into liquid nitrogen to further reduce the temperature proximate −120° C. The artificial insemination straws containing the reduced dose inseminate (3) can then transferred to liquid nitrogen to further reduce the temperature to −196° C. for storage.

A comparison of frozen thawed reduced dose inseminate (3) containing the combination of X-chromosome bearing bovine sperm cells (paternal sperm cells (1)) and horse sperm cells (heterogeneous sperm cells (4)) prepared as above described was compared with similarly prepared flow sorted X-chromosome bearing bovine sperm cells without the addition of pig sperm cells as to 0 hour motility (motility at immediately upon thawing), acrosome intactness, and total survival time after thawing (the duration of time having an end point based on the last to die sperm cell in a sample population).

TABLE 10

Comparison of Post Thaw Motility and Survival Time Between Reduced Dose Inseminate And Flow Sorted Sperm Cells.

| Inseminate | 0 Hour Motility | Survival Time |
|---|---|---|
| Reduced Dose Inseminate[1] | 54% | 10 hrs |
| Flow Sorted Bovine Sperm Cells[2] | 30%-40% | 4 hrs-6 hrs |

[1]Combination of flow sorted X-chromosome bearing bovine sperm cells (paternal sperm cells)(1M/0.25 mL) and horse sperm cells (heterogeneous sperm cells)(2M/0.25 mL).
[2]Flow sorted X-chromosome bearing bovine sperm cells (1M/0.25 mL).

Now referring to Table 10, which summarizes the results of a comparison of post thaw motility and survival time between a reduced dose inseminate (3) containing a combination of flow sorted bovine sperm cells (X-chromosome bearing sperm cells) and horse sperm cells prepared as above described and flow cytometry sorted bovine sperm cells (X-chromosome bearing sperm cells) without combination with horse sperm cells, but otherwise prepared as above described, it can be understood that the reduced dose inseminate (3) has a greater 0 hour motility and greater survival time.

Artificial insemination of 140 donor cows with a corresponding 140 0.25 mL artificial insemination straws each containing a reduced dose inseminate prepared as above described resulted in a conception rate of 54% (76/140) from which 73 female calves were born proving a 95% purity of the X-chromosome bearing population of bovine sperm cells achieved by flow sorting as above-described.

For the purposes of this invention the term "artificial insemination" refers to the process by which the "reduced dose inseminate" is placed into the reproductive tract of a female animal of the same species (8) as the paternal animal (2) for the purpose of impregnating the female animal (8). Without limitation to the forgoing, certain embodiments of the invention can utilize intracervical insemination where the "reduced dose inseminate" can be injected deep into the cervix. Other embodiments of the invention, can utilize intrauterine insemination of the "reduced dose inseminate" from which the sperm cells have been removed from most other components of the seminal fluids and can be injected directly into the uterus of the female animal. Yet other embodiments of the invention can include laparoscopic artificial insemination of the female animal of the same species (8) as the paternal animal (2).

For the purposes of this invention the term "in vitro fertilization" refers to the process by which an egg (6) of a female animal of the same species (8) as the paternal animal (2) can be fertilized using a reduced dose inseminate (3) which includes paternal sperm cells (1) outside of the womb, in vitro. The process can involve hormonally controlling the ovulatory process, removing ova ("eggs") (6) from the female animal's (8) ovaries and allowing paternal sperm cells (1) of the reduced dose inseminate (3) to fertilize them in a fluid medium. The egg(s) (6) removed from female animal's (8) ovaries and can be cryopreserved and later fertilized in vitro. The resulting embryos (42) can then be transferred to the uterus of recipient female animal(s) with the intent to establish a successful pregnancy or cryopreserved for later implantation.

For purposes of the present invention, "embryo" refers to the stages of development whereby a fertilized egg (6) obtained from a female animal of the same species (8) as the paternal animal (2) develops toward a fetus (42), in vitro or in vivo.

In particular embodiments of the invention, the heterogeneous sperm cells (4) may be provided to an end user in the form of a kit designed to allow the end user to combine a sample of paternal semen (1) of known or unknown concentration with said heterogeneous sperm cells supplied in the kit to create a plurality of reduced dose inseminates (3).

A particular non-limiting example of a kit to a create reduced dose inseminate (3) can be prepared by providing a 0.50 mL straw of cryopreserved bull (bovine) semen containing 200 million sperm cells from a bull that produces sperm which is unable to fertilize (infertile bull is heterogeneous sperm cells (4) source) and a vial containing 4.0 ml of sterile liquid dilution extender such as TALP, TRIS A, Androhep, Triladyl, or the like. The contents of said 0.50 mL straw of heterogeneous sperm (4) is placed in said vial containing 4.5 ml of sterile liquid dilution extender to create a diluted portion of heterogeneous sperm at concentration of about 20 million sperm per ml.

The end user of the kit provides a frozen straw of commercially available bovine semen (bull is paternal sperm (1) source) which is thawed to provide about 10 million paternal sperm (1) in a volume of about 0.50 ml.

The thawed about 10 million paternal sperm (1) can be placed into the vial containing about 5 mL of heterogeneous sperm (4) at about 20 million sperm per mL to generate a mixture containing about 2 million paternal sperm (1) and 20 million heterogeneous sperm cells (4) per ml.

The end user uses empty 0.5 mL cryopreservation straws to draw up about 0.5 mL of said mixture of paternal and heterogeneous sperm to provide a reduced dose inseminate (3) of a volume of about 0.5 ml containing about 1 million paternal sperm (1) and about 10 million heterogeneous sperm (4). Since the end user is able to fill about 10 of said empty 0.5 mL cryopreservation straws, the number of usable reduced dose inseminates (3) provided by the kit is about 10 times greater than the number of paternal sperm (1) straws originally thawed. In this way, the number of breedings from a genetically valuable bull can be increased by a multiple.

For the purpose of the present invention, the term "combination or combining or combined" refers to any method of putting two or more materials together. Such methods include, but are not limited to, mixing, commingling, incorporating, intermingling, stirring, integrating, or the like.

For the purposes of the present invention, ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a sperm cell" refers to one or more of sperm cells. As such, the terms "a" or "an", "one or more" and "at least one" can be used interchangeably herein unless otherwise indicated. According to the present invention, an isolated material or particle is removed from its natural milieu; however, an isolated material does not necessarily reflect the extent to which the material or particle has been purified.

As can be easily understood from the foregoing, the basic concepts of the present invention may be embodied in a variety of ways. The invention involves numerous and varied embodiments of a reduced dose inseminate (3) and methods of making and using such a reduced dose inseminate (3). As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "flow sorter" should be understood to encompass disclosure of the act of "flow sorting" whether explicitly discussed or not and, conversely, were there effectively disclosure of the act of "flow sorting", such a disclosure should be understood to encompass disclosure of a "flow sorter" and even a "a means for flow sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Thus, the applicant(s) should be understood to claim at least: i) each of the reduced dose inseminates herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof or to obtain any benefit of reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

In addition, the claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method of producing an inseminate comprising:
   a) obtaining a plurality of sex-selected bovine sperm cells;
   b) obtaining a plurality of heterogeneous sperm cells, wherein the heterogeneous sperm cells comprise either a plurality of sperm cells obtained from a species other than bovine, or a plurality of infertile bovine sperm cells;
   c) combining said plurality of heterogeneous sperm cells with said plurality of sex-selected bovine sperm cells;
   d) providing within a combination of said sex-selected bovine sperm cells and said heterogeneous sperm cells a plurality of sex-selected bovine sperm cells sufficient to achieve fertilization of a bovine egg.

2. The method of claim 1, further comprising the step of fertilizing said bovine egg in vivo with said combination of sex-selected bovine sperm cells and heterogeneous sperm cells.

3. The method of claim 2, further comprising the step of artificially inseminating a female bovine with said combination of sex-selected bovine sperm cells and heterogeneous sperm cells.

4. The method of claim 3, further comprising the step of achieving a pregnancy of said female bovine by artificially inseminating said female bovine with said combination of sex-selected bovine sperm cells and heterogeneous sperm cells.

5. The method of claim 4, further comprising the step of producing a bovine offspring from said pregnancy of said female bovine.

6. The method of claim 1, further comprising the step of providing in said combination fewer of said plurality of sex-selected bovine sperm cells as compared to said plurality of heterogeneous sperm cells.

7. The method of claim 6, further comprising the step of allocating to said combination said plurality of sex-selected bovine sperm cells in a range of about five percent to about fifty percent of said plurality of heterogeneous sperm cells.

8. The method of claim 1, wherein said plurality of heterogeneous sperm cells comprise a plurality of sperm cells obtained from a species other than bovine and are incapable of fertilizing said bovine egg.

9. The method of claim 1, wherein said plurality of heterogeneous sperm cells comprise infertile bovine sperm cells incapable of fertilization of said bovine egg.

10. The method of claim 1, further comprising the step of mixing said plurality of sex-selected bovine sperm cells with an amount of TRIS A extender to achieve a concentration of said plurality of sex-selected bovine sperm cells in a range of about 8 million per mL to about 16 million per mL.

11. The method of claim 10, further comprising the step of mixing with said plurality of heterogeneous sperm cells an amount of TRIS A extender to achieve a concentration of said plurality of heterogeneous sperm cells in a range of about 32 million per mL to about 48 million per mL.

12. The method of claim 1, wherein said step of combining said plurality of heterogeneous sperm cells with said plurality of sex-selected bovine sperm cells results in a concentration of sex-selected bovine sperm cells in a range of about 4 million sperm cells per mL and about 8 million sperm cells and a concentration of said heterogeneous sperm cells in a range of about 16 million sperm cells per mL and about 24 million sperm cells per mL.

13. The method of claim 12, further comprising the step of adding an amount of TRIS B to achieve a concentration of sex-selected bovine sperm cells in a range of about 2 million sperm cells per mL and about 4 million sperm cells and a concentration of heterogeneous sperm cells in a range of about 8 million sperm cells per mL and about 12 million sperm cells per mL.

14. The method of claim 13, further comprising the step of providing an artificial insemination dosage comprising an artificial insemination straw having a volume in a range of about 0.25 mL and about 0.5 mL which contains sex-selected bovine sperm cells in a range of about 0.5 million to 2 million and heterogeneous sperm cells in a range of 2 million to about 6 million.

15. The method of claim 14, further comprising the step of freezing said artificial insemination dosage.

16. The method of claim 14, further comprising the step of thawing said artificial insemination dosage.

17. The method of claim 14, wherein said TRIS A comprises TRIS A2, and wherein said TRIS B comprises TRIS B2.

* * * * *